United States Patent
Lewis et al.

(10) Patent No.: US 8,919,960 B2
(45) Date of Patent: Dec. 30, 2014

(54) ADAPTIVE INFRARED RETINOSCOPIC DEVICE FOR DETECTING OCULAR ABERRATIONS

(76) Inventors: James Waller Lambuth Lewis, Tullahoma, TN (US); Ming Wang, Nashville, TN (US)

( * ) Notice: Subject to any disclaimer, the term of this patent is extended or adjusted under 35 U.S.C. 154(b) by 807 days.

(21) Appl. No.: 12/762,643

(22) Filed: Apr. 19, 2010

(65) Prior Publication Data

US 2010/0201944 A1 Aug. 12, 2010

Related U.S. Application Data

(63) Continuation-in-part of application No. 11/642,226, filed on Dec. 20, 2006, now abandoned.

(60) Provisional application No. 60/751,781, filed on Dec. 20, 2005.

(51) Int. Cl.
- *A61B 3/00* (2006.01)
- *A61B 3/10* (2006.01)
- *G06T 7/00* (2006.01)
- *A61B 3/103* (2006.01)

(52) U.S. Cl.
CPC ............... *A61B 3/103* (2013.01); *G06T 7/0012* (2013.01); *G06T 2207/20056* (2013.01); *G06T 2207/30041* (2013.01); *G06T 2207/10048* (2013.01)
USPC ............................ 351/212; 351/200; 351/221

(58) Field of Classification Search
CPC .......... A61B 3/1015; A61B 3/14; A61B 3/13; A61B 3/156; G02B 21/0012; G02B 21/361; G02B 21/365
USPC ......... 351/200, 205, 206, 211–213, 221, 222, 351/208, 209, 243; 600/310, 356, 383, 400, 600/558
See application file for complete search history.

(56) References Cited

U.S. PATENT DOCUMENTS

| | | | | |
|---|---|---|---|---|
| 5,797,046 | A | * | 8/1998 | Nagano et al. ................... 396/51 |
| 2001/0037105 | A1 | * | 11/2001 | Lin .................................... 606/5 |
| 2003/0044174 | A1 | * | 3/2003 | Endo ............................... 396/55 |
| 2004/0189942 | A1 | * | 9/2004 | Yoon .............................. 351/221 |

* cited by examiner

*Primary Examiner* — Thomas K Pham
*Assistant Examiner* — Brandi Thomas
(74) *Attorney, Agent, or Firm* — Hornkohl Intellectual Property Law, PLLC; Jason L. Hornkohl

(57) ABSTRACT

An ocular system for detecting ocular abnormalities and conditions creates photorefractive digital images of a patient's retinal reflex. The system includes a computer control system, a two-dimensional array of infrared irradiation sources and a digital infrared image sensor. The amount of light provided by the array of irradiation sources is adjusted by the computer so that ocular signals from the image sensor are within a targeted range. Enhanced, adaptive, photorefraction is used to observe and measure the optical effects of Keratoconus. Multiple near-infrared (NIR) sources are preferably used with the photorefractive configuration to quantitatively characterize the aberrations of the eye. The infrared light is invisible to a patient and makes the procedure more comfortable than current ocular examinations.

10 Claims, 11 Drawing Sheets

Cortex cataract
(-0.5,0,0) 20/25+

Tear-film breakup
in eccentric PR image

ADAPTIVE INFRARED RETINOSCOPIC DEVICE FOR DETECTING OCULAR ABERRATIONS

CROSS-REFERENCES TO RELATED APPLICATIONS

This application is a Continuation-In-Part which claims priority from U.S. Utility patent application Ser. No. 11/642,226 filed Dec. 20, 2006, entitled "ADAPTIVE INFRARED RETINOSCOPIC DEVICE FOR DETECTING OCULAR ABERRATIONS", which claims priority from U.S. Provisional Patent Application Ser. No. 60/751,781 filed Dec. 20, 2005, entitled "INFRARED RETINOSCOPIC DEVICE FOR DETECTING CORNEAL IRREGULARITIES AND OCULAR OPTICAL OPACITIES" which are hereby incorporated by reference.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

FIELD OF THE INVENTION

The present invention is generally related to the providing of medical ocular assistance and examination. More particularly, the present invention is directed toward an ocular inspection technique and apparatus.

BACKGROUND OF THE INVENTION

Keratoconus (KC) is the most common corneal dystrophy in the U.S. and affects one in every 500 to 2000 Americans. This ocular condition involves progressive corneal thinning that eventually causes an outward bulging of the cornea. KC is often misdiagnosed as myopia and astigmatism. In a study of 91 patients seeking keratorefractive surgery, 5 cases (5.5%) were identified as KC from a topography examination. The onset of KC typically occurs in teenagers and adults in their 20s. The NIH/NEI Collaborative Longitudinal Evaluation of Keratoconus (CLEK) Study is a prospective, observational study of 1,209 KC patients whose purpose is to characterize the changes in vision, corneal curvature and scarring and quality of life of the Keratoconus patients and to better understand the variation of these measures over time. The typical age of onset of the condition, its long duration and the importance of vision to life functions increase the importance of diagnosing KC as a disease. In fact, studies have shown that the impact of KC on quality of life indicators extends far beyond what one might expect from the loss of visual acuity alone. Previously, treatment options were quite limited and usually relied upon the proper selection and constant fitting of rigid gas-permeable contact lens during the disease's progression. As a result, the advantages gained by the detection of mild or early stage form of KC, Forme Fruste Keratoconus (FFKC), were limited. However, comparatively recent developments in ophthalmic cornea treatments have altered this situation. Specifically, new treatment options now exist for FFKC and KC that suggest clear potential advantages for early diagnosis of patients. Furthermore, the increasingly popular use of LASIK and PRK makes detection of FFKC quite important to minimizing the potential of undesirable surgical outcomes. KC must be detected and quantified in the earliest stage possible to understand the disease's progression and to determine the best treatments for affected patients.

Two new treatments for Keratoconus and corneal ectasia, surgery-resulted Keratoconus, are corneal collagen cross linking with Riboflavin (C3-R) and Intacs intracornea rings. C3-R strengthens the corneal integrity by cross-linking the collagen fibrils together using Riboflavin. It has successfully halted, and in some cases even reversed, KC progression when performed during early stages of the disease. Intacs corneal inserts or implants are a minimally invasive surgical option wherein two tiny, clear crescent-shaped pieces of a plastic polymer are inserted into the cornea. Intacs flatten the steep part of cornea area, correct the myopic refractive error and reduce vision distortion. These treatments are especially advantageous because no cornea tissue is removed and there is no ablation or incision across the visual axis. Since these two new methods can stop or slow the progression of the disease and both provide improved visual function, early methods of detecting FFKC are more important than ever.

The existence of KC and FFKC is known to be a significant concern and most likely a contraindication for certain cornea surgery methods, such as LASIK. The Cataract and Refractive Surgery Today journal has reported several high profile lawsuits filed by FFKC patients who experienced bad outcomes following laser cornea surgery. As the popularity of laser cornea surgery increases, it is advantageous to be able to detect FFKC and early-stage KC to reduce or eliminate such surgical complications. Currently, pre-surgery LASIK patients typically undergo a clinical examination by a medical professional for indications of KC. These clinical methods include retinoscopy, slit lamp examination, indirect opthalmoscope, and handheld keratoscope. A second type of examination that uses corneal surface imaging systems is also utilized. Common cornea surface imaging instruments include Orbscan II, Humphrey Atlas, EyeSys, and Tomey TMS-4. Even with these detection methods, short-comings exist for accurate and sensitive detection of FFKC that limit the opportunities for confident clinical and large-population FFKC screening.

Around the world, experienced physicians are aware of the irregular retinal reflex appearances from high-order ocular aberrations, including KC, which may be observed using hand-held photorefractive retinoscopes. Prior to computerized testing methods such as autorefraction, the retinoscope was the main method for objective measurement of refractive error and identification of irregular astigmatism. Shortcomings of current retinoscopes include the broad-spectrum of the light sources used that integrates chromatic aberration in the measurement and the visible irradiation that stimulates pupil response and hence, in a non-mydriatic examination, reduces the examined pupillary area. Furthermore, current retinoscopic observations cannot be stored in digital form for discussion and sharing.

Photorefraction (PR) is a technique that shares similar optical features with retinoscopy but does not use a beam splitter. Photorefraction techniques can be used to create a retinal reflex image that depends upon the optical properties of the eye. However, current photorefraction techniques create poor quality images of the retinal reflex that cannot be used to detect high-order aberrations such as astigmatism which are quite common. Thus, Current PR refractive diagnostics typically produce poor readings and results and the PR technique is currently only utilized for eccentrically illuminated detection of refractive errors.

Therefore, what is needed is a new method of identifying high-order ocular aberrations such as FFKC and early-stage KC to help avoid laser cornea surgery complications and to offer the best treatment options for the largest number of individuals having these aberrations.

BRIEF SUMMARY OF THE INVENTION

An embodiment of the present invention is directed toward a retinoscopic-like device for detecting high-order ocular aberrations. The device includes at least one light source that produces infrared light. An optical beam splitter is positioned such that the infrared light is directed from the light source into a patient's eye to form a point of light on the patient's retinal and reflected by the patient's retina into an image sensor such as a digital infrared camera. The image sensor detects the infrared light and produces a photorefractive image based upon the detected infrared light. The optical beam splitter is adjustable such that coaxial and eccentric photorefraction images of the patient's eye can be obtained through the adjustment. The light source may be an array of light sources positioned in a plane such that coaxial and eccentric images can be obtained in rapid sequence without the need to adjust the beam splitter. The beam splitter and the light sources are positioned such that the distance between the beam splitter and the light sources is approximately equal to the distance between the beam splitter and an entrance pupil of image sensor. A screen instantaneously displays the infrared photorefractive images captured by the image sensor. A computer automatically adjusts an intensity of the light produced by the lights or a sensitivity of the camera based upon a (pre-probed) detected image. Software stores multiple photorefractive images and digitally analyzes the images to identify ocular abnormalities or conditions.

Another embodiment of the present invention is directed toward a method of providing ocular examination of cornea irregularities and ocular optical opacities. In accordance with the method, an infrared light is directed into the patient's eye with an optical beam splitter. The infrared light is focused to a point on the patient's retina, reflected off of the patient's retina and diffracted through the ocular elements, or is scattered by any structure that is in the optical pathway or on the ocular elements, and into a digital camera that can detect infrared light. A photorefractive digital image of the retinal reflex is produced based upon the detected infrared light. The infrared light source, the camera and the optical beam splitter are aligned to project an irradiation source plane into an entrance pupil plane of the camera. The optical beam splitter is adjusted along an axis between the light source and the camera to produce coaxial and eccentric photorefraction images of the patient's eye. According to the location of each illumination source relative to the optical axis of the camera, the entrance pupil of camera selects a related portion of ocular wavefront information in each acquired photorefractive image. The images are displayed in real time for review by an operator. The image is digitally saved in an automatically created patient file. The camera is preferably focused to acquire photorefractive images from at least two ocular depths or surfaces of interest. A trial lens may be used in front of the eye to compensate for refractive error, accommodation, and system working distance. A condensing lens may be used in front of the eye to increase the illumination field angle on a retina surface to also acquire a fundus image. The coaxial image is preferably used to determine a retinal reflectance of the eye and the reflectance is used to calculate required irradiation intensities for consequent eccentric images. The acquired images are subjected to Fourier analysis to identify ocular conditions. Image correlation analysis is performed between photorefractive images acquired at different times to differentiate between transient and stationary ocular conditions through image correlation analysis. Tear film break-up time is determined by detecting a dynamic change in at least one selected eccentric image.

DETAILED DESCRIPTION OF THE INVENTION

Figure 1:
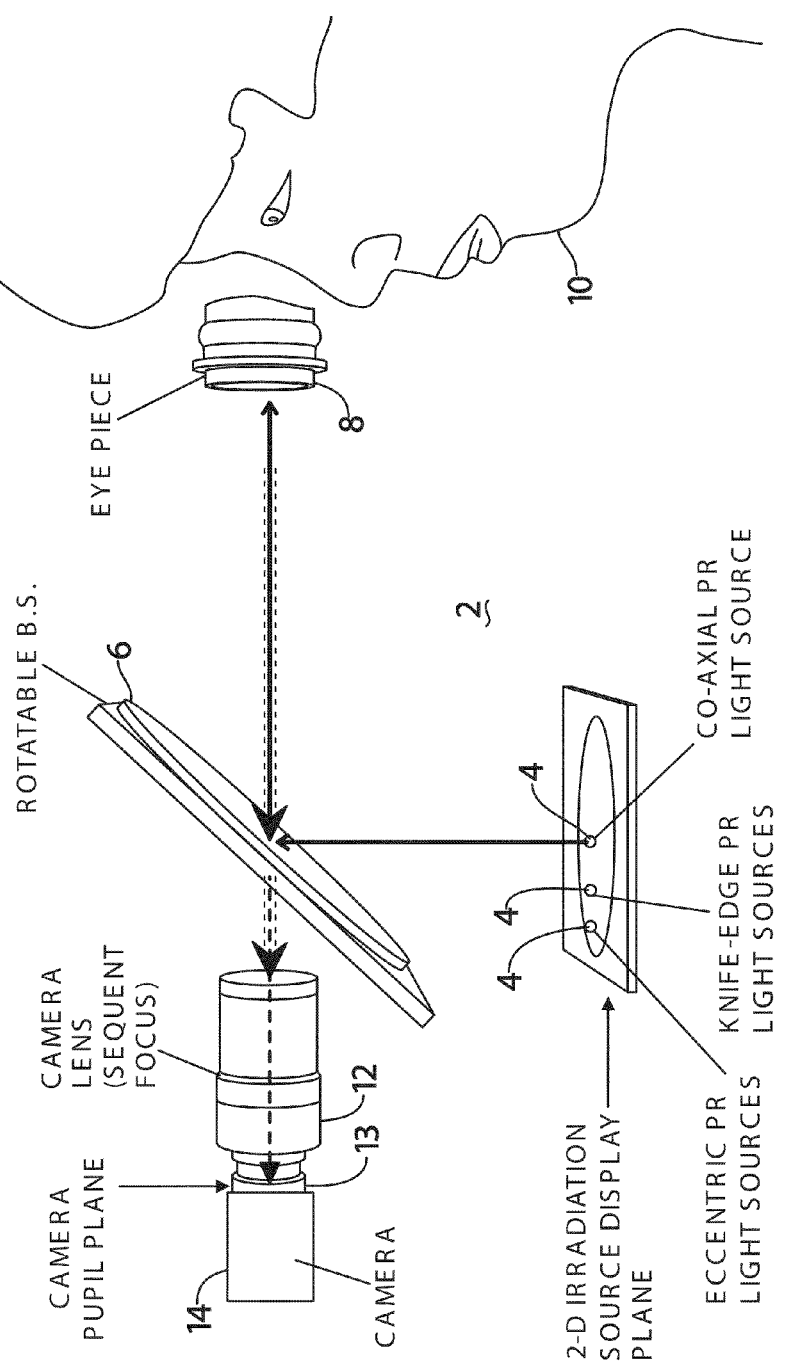
FIG. 1 is a diagram of an infrared photorefractive ocular instrument constructed in accordance with an embodiment of the present invention.

A multi-axis infrared photorefractive retinoscope constructed in accordance with an embodiment of the present invention combines simple hardware with smart software control and smart design to provide improved detection of ocular aberrations. In the present invention, photorefraction is accomplished by delivering an infrared light beam into the eye of a patient where it is bent by the ocular properties of the eye, hits the retina, and then reflects back to the camera and is detected as an image. The light is directed into the eye so that it is naturally focused to a point on the patient's retina by the eye's cornea and crystalline lens so that the photorefractive image received and produced by the camera is not an image of the surface of the retina. Rather, the photorefractive image is an image of the retinal reflex which appears on the pupil plane. This pupil image appearance depends upon the ocular properties of the eye, not the appearance of the retina itself.

An optimal hardware design was arrived at through the use of new anatomically accurate, disease-eye modeling simulation methods. The disease-eye models used included the anterior and posterior corneal topographies together with the ocular parameters obtained from ultrasonic biometry. The lens surface parameters were iterated to produce a measured total ocular wavefront aberration map. The patient visual performance and photorefraction measurement predictions were then evaluated for various optical settings. The optical system design is thus optimized for disease detection. The control software uses a new feedback method to obtain photorefractive retinoscope images with the best possible dynamic range for each individual patient. The simple hardware plus smart software concept makes low-cost, efficient, large scale ocular screening achievable. It also allows for new quantitative measurement analysis techniques and methods.

An embodiment of the present invention is readily adaptable into a low cost, robust, and easy to construct, align, and maintain system. The system utilizes three main improvements over typical photorefractive and retinoscopic techniques: 1) near-infrared (NIR), narrow-band spectral light sources allow non-intrusive, low-intensity illumination and scotopic ocular examination without eye drops; 2) the combination of a beam splitter and an array of light sources allows multiple-meridian, multiple-eccentricity, photorefractive detections with co-axial photorefraction for self-calibration and; 3) a high speed, multi-frame digital camera sensitive to infrared light allows dynamic analysis of an ocular temporal profile. In a darkened testing room, use of the NIR light emitting diodes (LEDs) requires no pupil dilation, which is contrary to current retinoscopy, opthalmoscope, photo screening, and slit-lamp examinations. Since the retina reflectance is much higher in the NIR than the visible region, the required NIR irradiation is much lower and safer to obtain sufficient signal level. Monochromatic NIR sources avoid the ambiguity of polychromatic aberrations produced by some prior art devices and enable non-mydriatic examination of a larger visual zone in a darkened testing environment. Invisible NIR light does not stimulate pupil response and is much more comfortable for patients. Small LEDs and fiber optics enable the expansion of a single light source into a 2-dimensional light source array. The optical beam splitter directs the light from each of the light sources to a point on the retina and directly inside the camera entrance pupil. This allows on- and near-axis illuminated photorefraction images as well as highly sensitive knife-edge images to be taken with a high degree of spatial control. The multiple-meridian and -eccentricity illuminations dramatically increase the detection sensitivity of the device. A high-speed digital camera provides enhanced information over a single-shot camera by acquiring many images over a short period of time. The above described hardware improvements allow ocular aberration characteristics to be extracted by decoupling the mixed and ambiguous information obtained from typical photorefraction and retinoscopic methods.

Referring now to FIG. 1, a photorefractive ocular instrument constructed in accordance with an embodiment of the present invention is shown. The ocular instrument 2 consists of an array of light emitting diodes 4 (LEDs) positioned below an optical beam splitter layer 6 that reflects the light from the LEDs 4. While infrared LEDs 4 are preferred, any suitable light source including optical fibers may be used if desired. The reflected light from the beam splitter 6 is directed through an eye piece 8 into an eye of a patient 10. The array of LEDs 4 allow light to be reflected to coaxially and eccentrically into the patient's eye. Alternatively, a single LED 4 can be used and the beam splitter 6 rotated and tilted to reflect the light towards the patient's eye. The light sources 4 and the camera 12 positions can be switched with respect to the beam splitter. A small portion of the light directed toward the eye of the patient 10 is reflected and scattered backward when it hits the ocular elements' surfaces or any imperfection in the ocular light path. A major portion of the light entering the eye is focused to a spot on the patient's retina by the optical elements of the patient's eye, diffusively reflected from the retina, diffracted by the lens and cornea on the return path, and emitted from the eye toward the camera lens 12. After it passes through the beam splitter 6, the camera lens 12 and associated camera 14 capture a portion of the scattered light and the double-pass retinal reflex. The entrance pupil 13 of the camera 12 is the effective aperture of the detection. The camera lens 12 focuses the light and forms a pupil image on the camera 14. A rapid collection of these images can be used to diagnose a variety of ocular conditions as described in more detail herein below.

Figure 2:
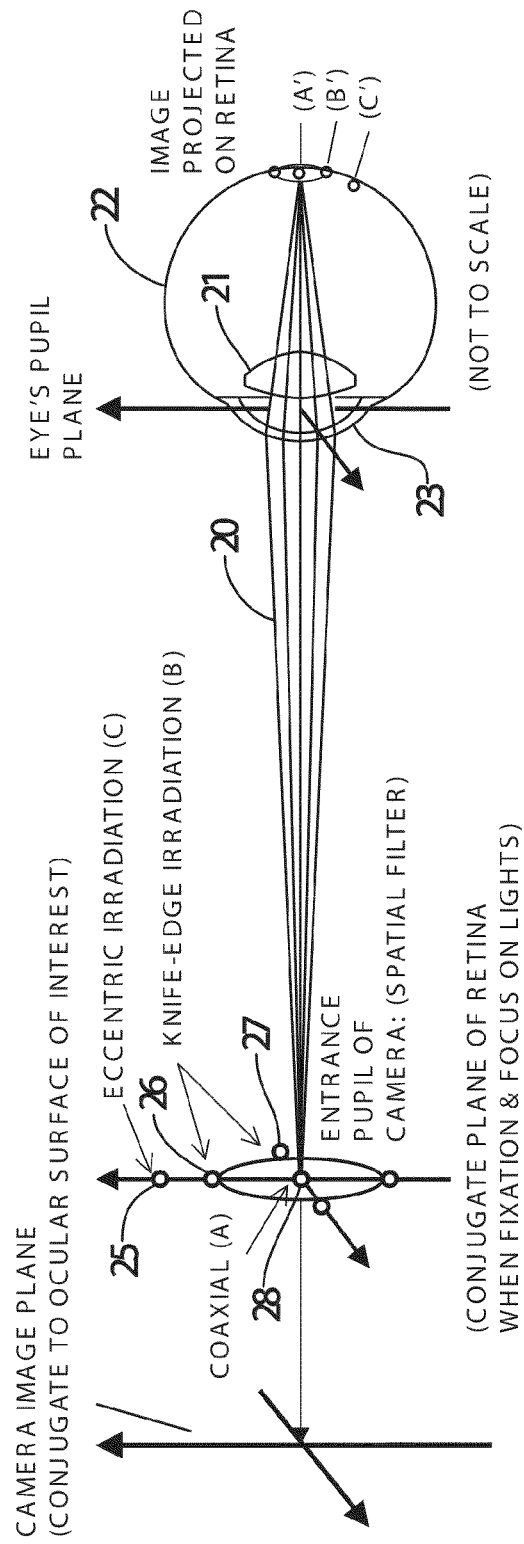
FIG. 2 is a diagram illustrating the reception of the light from the different light sources by the instrument of FIG. 1.

Referring now to FIG. 2, a diagram illustrating the reception of the light by the camera of FIG. 1 is shown. The light 20 from a coaxial light source 28 which is focused to a spot on the patient's retina 22 and reflected by the retina 22 passes through the cornea 23 and lens 21 of the patient's eye and into the entrance pupil 24 of the camera. When the examined eye is focused on the light source plane, the light source plane is conjugate to the patient's retina 22. For an ideal eye, the light from each of the small infrared LED's in the array forms a tiny point on the retina and then is diffusively reflected back toward its initial light source location 25, 26, 27, or 28. For an actual eye, the intensity distribution of light at this conjugate location is described by the double-pass point spread function (PSF) of the eye. Since the beam splitter is aligned to project the light source plane onto the camera's entrance pupil plane, this double-pass PSF falls onto the plane of camera pupil 24. The effective camera entrance pupil acts as a spatial filter that allows only light rays inside the aperture to be focused by the camera lens and to contribute to the eye image. For a normal healthy eye, the PSF is a small spot. If the illumination source is inside the camera pupil (coaxial and semi-coaxial), the reflex will totally pass the aperture and the pupil image will be evenly bright. If the illumination is outside of the camera pupil (eccentric), the returned reflex will be blocked and the pupil image will be all dark. For an aberrative eye, only the ocular wavefront $W(x, y)$ that is convergent toward the camera aperture will be captured and contribute to the pupil image. The wavefront aberration that can be detected includes the direct scattered light from the ocular imperfections, the diffracted light from the irregular ocular surfaces, and the retro-illumination of the patient's eye that identifies optical opacities through the optical path of the eye. The correlation between the light source location and the camera pupil enables spatial frequency filtering and effectively captures high-order (HO) aberrations.

The infrared light used is invisible to the patient and, thus, much more comfortable than the conventional visible spectrum lights used in current ocular instruments. When performing tests in the dark, a patients' pupil is naturally dilated. Infrared light will not stimulate the pupil response so no eye drop is required. Because the retinal reflectance in the infrared region is much stronger than in the visible region, much less irradiation is needed for a sufficient signal level. In addition, since the light is focused to a narrow point, there is no need for a wide dilated pupil for the light to pass through. Therefore the procedure is safe, noninvasive, and comfortable to the patient.

Figure 3:
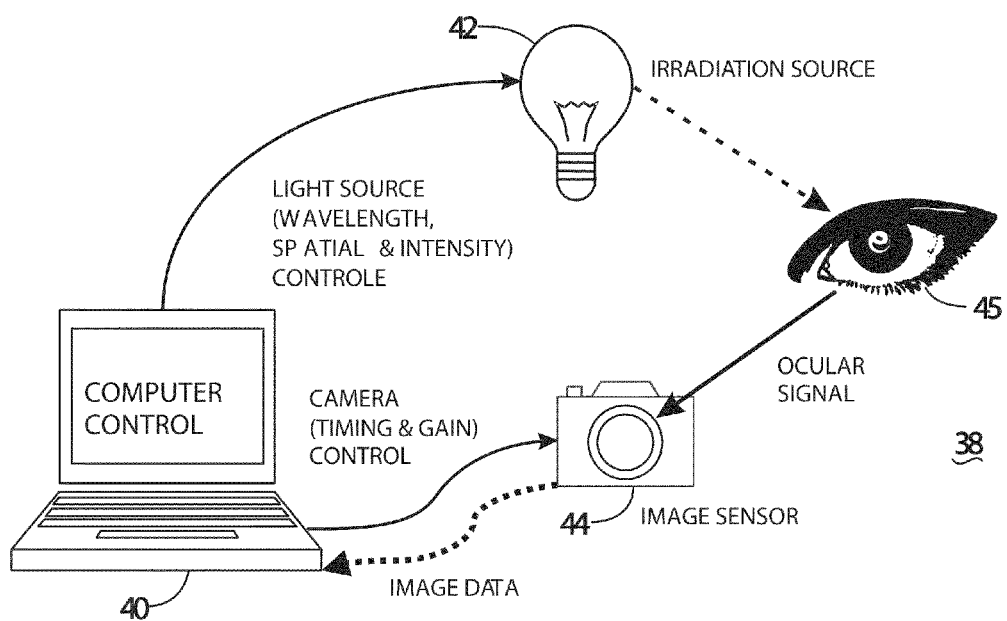
FIG. 3 is a block diagram of a computer system for analyzing the results of the infrared photorefractive measurements taken with the ocular instrument of FIG. 1.

Referring now to FIG. 3 a block diagram of a system 38 for analyzing the results of measurements taken with the ocular instrument of FIG. 1 is shown. The system includes a computer 40 and an irradiation system 42 that provides multiple meridian and eccentricity illuminations at selected wavelengths based upon instructions received from the computer 40. The computer instructs the irradiation system 40 and the image sensor 44 to provide the specified irradiation characteristics and detection sensitivity based on the ocular signal level received from the examinee's eye 45. The computer control system 40 then analyzes the captured images and provides results of the in-situ analysis to an optical technician. The use of a digital camera 44 as the photorefractive image detection system allows a digital recording to be made of the images and, thus, provides for detailed records of the patient's eye and the examination. Digital registration of the images facilitates computer-based analysis and extraction of the image's maximum information content, and enables telemedicine applications. In addition, the digital images can be subjected to quantitative, Fourier analysis to detect higher order aberrations.

The computer system 40 preferably utilizes smart software control methods to control the photorefractive image acquisition process. In particular, the computer 40 preferably functions as a data acquisition device and allows for precise control of the light source 42 as well as the camera's 44 exposure time and signal magnification. The smart software acquires personal data concerning the patient's age, gender, race, refraction, and the detected coaxial signal level and uses this information to precisely control the camera's 44 sensitivity and the amount of illumination provided from the light sources 42 to obtain the best possible images. The computer 40 uses the subject's race to initialize the light source 42 and camera 44 image acquisition settings. Race affects the images due to its influence on the reflectance of a patient's retina. The computer 40 then uses feedback programming methods to obtain higher-quality data by iteratively controlling the acquisition settings. The feedback used includes the detection parameters and pupil image information. The light source's 42 irradiance and pulse time are varied to optimize the pupil image's background pixel level and dynamic pixel range and avoid image saturation and under exposure. This smart control eliminates the low quality data that is typically obtained from single shot ocular instruments. Thus, the smart software of a preferred embodiment of the present invention automatically adapts the camera settings and lighting parameters to create optimal image data for each patient.

Once the photorefractive optical images have been acquired, computer-assisted image analysis is used to identify ocular aberrations. Target finding algorithms are utilized to identify and then extract the pupil area in each PR image. Image correlation algorithms are applied to multiple acquired images to eliminate non-stationary defects such as tear film breakup and floaters as described in more detail herein. Vector gradients, the first derivatives or slope of intensity distributions, are employed to identify second-order aberrations such as astigmatism. Fourier based image analysis techniques are used to extract the high spatial frequency elements and the corresponding high-order aberration properties. This analysis procedure helps to determine HO aberration indexes from the photorefraction technique. Diseased eye modeling and simulation from clinical test results can be compiled based upon the results and the breakdown in different spatial frequencies and indexes further helps in the identification of various ocular abnormalities.

Figure 4:
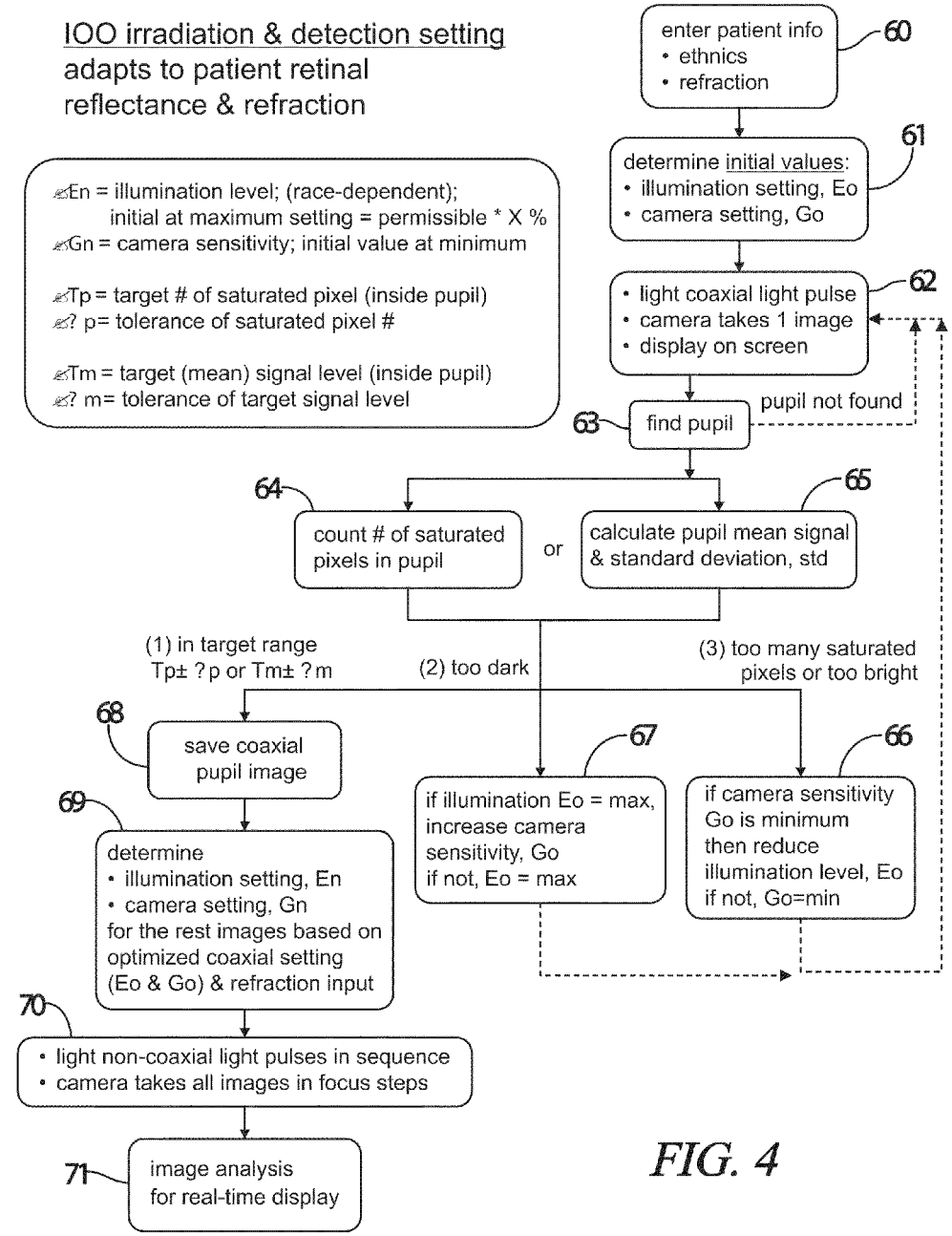
FIG. 4 is a flow chart of a method of adjusting the illumination levels and camera sensitivity of a system constructed in accordance with an embodiment of the present invention is shown.

Referring now to FIG. 4, a flow chart of a method of adjusting the illumination levels and camera sensitivity of a system constructed in accordance with an embodiment of the present invention is shown. Adaptive illumination and detection provides for optimal sensitivity. The method commences in step 60 with the entering of relevant patient data such as the patient's ethnicity and ocular refraction data into the computer system. The method then proceeds to step 61 wherein initial values such as the illumination settings and camera sensitivity are determined. The initial illumination settings preferably depend upon the subject's ethnicity while the camera sensitivity is preferably initially set to a minimum predetermined level. In step 62, a coaxial light pulse is produced while a photorefractive image of the retinal reflex is taken by the camera. The photorefractive image is displayed on a screen while an automated target finding algorithm is utilized to locate the subject's pupil as shown in step 63. The procedure is repeated by repositioning the setup until the pupil is located. Once the pupil is located, the method proceeds to count the number of saturated pixels inside the pupil in step 64 or calculate a mean pupil signal and standard deviation in step 65 depending upon the particular embodiment being utilized. If the analysis of the pupil image indicates that there are too many saturated pixels because the image is too bright, the method proceeds to step 66 wherein either the camera sensitivity or illumination level is reduced. If the image is too dark, the method proceeds to step 67 wherein either the camera sensitivity or illumination level is increased. In either situation, once the adjustments have been made, the method returns to step 62 to acquire a new image of the pupil with the configuration settings. If the pixel brightness is within a target range, the method proceeds to step 68 wherein the coaxial pupil image is saved. In step 69, an illumination and camera setting for the rest of the images is determined based upon the optimized coaxial setting and the patient's refraction input. In step 70, the non-coaxial lights are lit in sequence with the determined camera and illumination settings and images are taken in multiple focus steps with the camera and saved for each light. The adaptive procedure 62-67 may be applied to each non-coaxial image. The method ends in step 71 with image analysis performed on the images in real time as discussed in more detail herein.

Figure 5A:
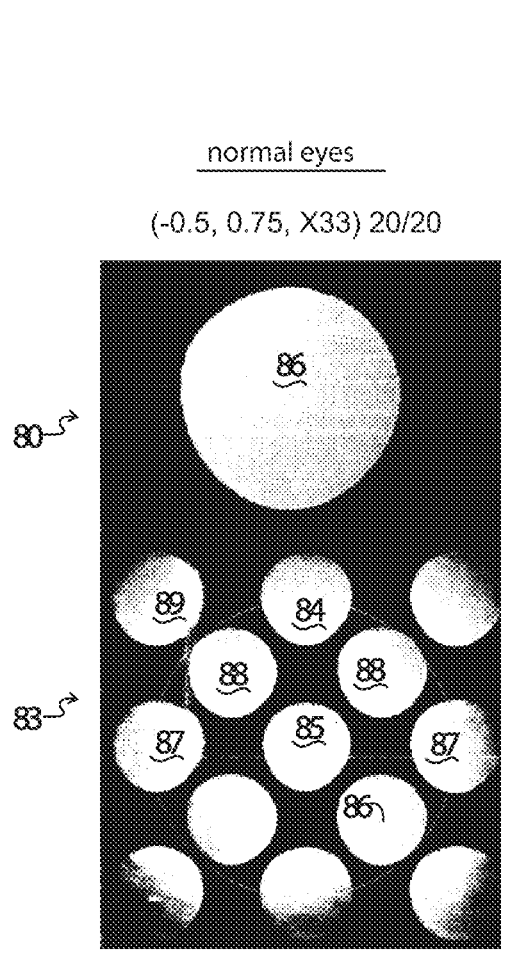
FIGS. 5(a) and (b) are illustrations of displays of eye image array data obtained for two healthy eyes using the ocular instrument of FIG. 1.
Figure 5B:
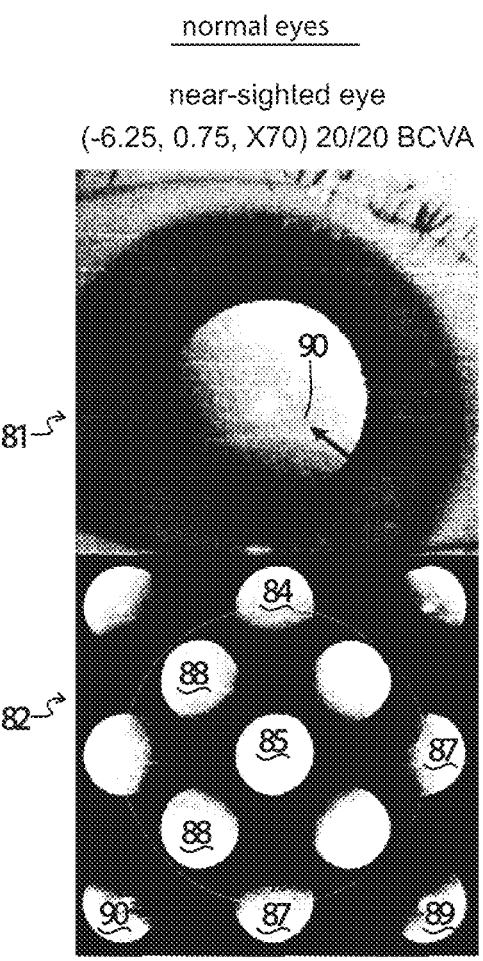

Referring now to FIGS. 5(*a*) and (*b*), illustrations of displays of photorefractive eye image array data obtained for two healthy eyes using the ocular instrument of FIG. 1 are shown. FIG. 5(*a*) and FIG. 5(*b*) each respectively show a large eye image 80 and 81 and eye image arrays 82 and 83. Each cropped pupil image 84 in the image arrays 82 and 83 corresponds to a digital picture of the retinal reflex of the eye taken with a different infrared LED lit. The device of FIG. 1 preferably takes 13 images 84 in 1-2 seconds. The computer program locates the pupil in each image 84, crops it, re-scales the pupil intensity, and combines all 13 images on screen in real-time. One large, unprocessed image 80 and 82 out of 13 is selected for improved visualization. This allows an individual to see the iris and examine any visible abnormal signs as well. As can be seen in the eye image arrays 82 and 83 for the eyes, the eye images 84 and the gradient variation are substantially symmetric about the central image 85. Other than the cornea reflection 86 at the center of each photorefractive image, there are no spots or deformations that correspond to the high-frequency variations observed in unhealthy eyes. This indicates that the patient's eyes are healthy and only the symmetric terms of second-order aberrations exist. The second-order terms include defocus from un-neutralized spherical refractive error, accommodation, and instrument convergence. The outward and inward gradient feature in the right 82 and the left 83 set of images indicate a near-sighted 82 and a very mild far-sighted 83 eye respectively. The patients whose eyes are shown in FIG. 5 are not suffering from HO aberrations from irregular cornea surfaces. The coaxial-photorefraction images 81 provide retinal reflectance self-calibration by providing a base reflectance level for use in acquiring the eccentric images. The knife-edge 87 and near knife edge 88 photorefractive images provide sharper HO-aberration information concerning irregular cornea shape, tear quality and optical opacities. The far eccentric 89 photorefractive images have a much less direct retro-illumination signal. They provide more clearly scattered light information from the anterior chamber including from various depths in cornea. A moving tear wave 90 is visible in the images of the nearsighted eye of FIG. 5(*b*).

Figures 6A, 6B:
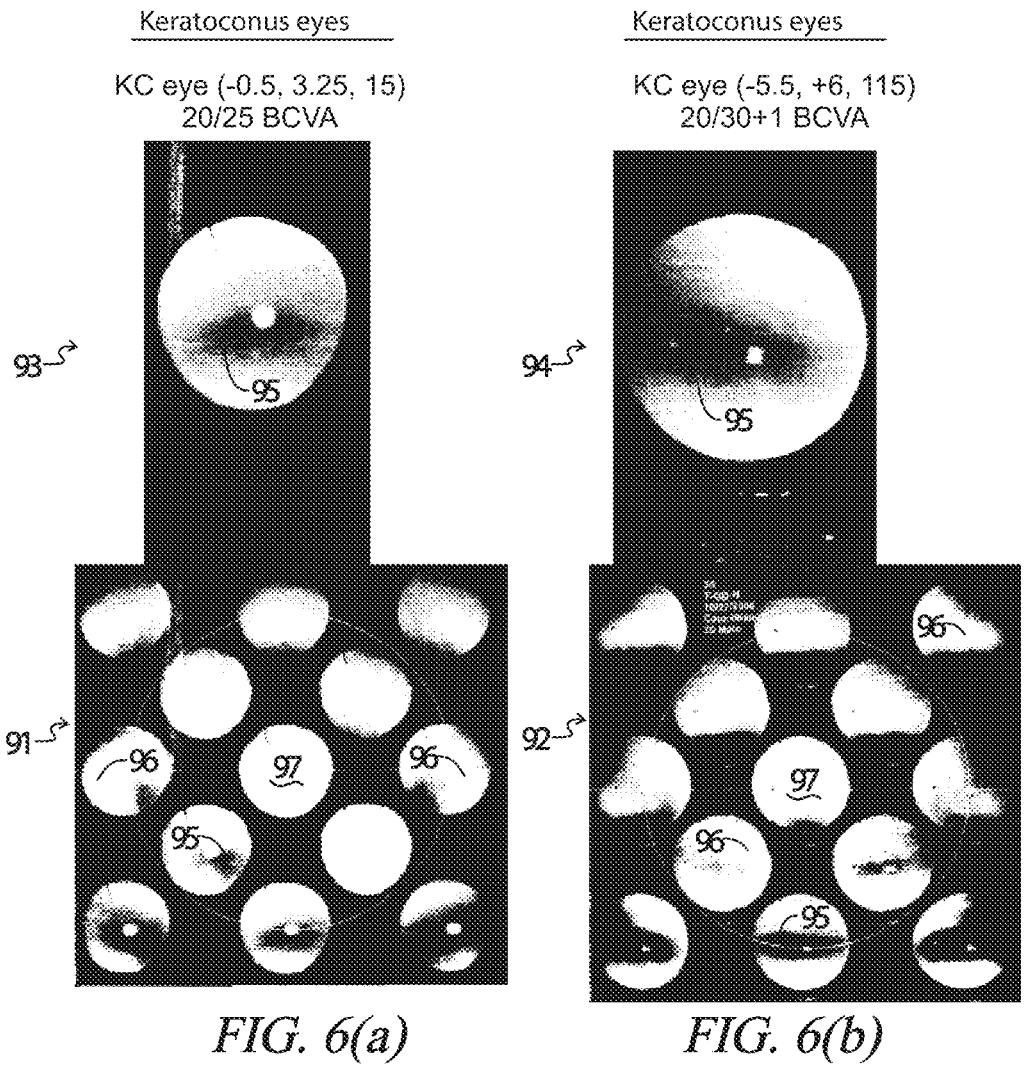
FIGS. 6(a) and (b) are illustrations of displays of eye image array data obtained for two eyes having keratoconus using the ocular instrument of FIG. 1.

Referring now to FIGS. 6(*a-b*), illustrations of displays of photorefractive retinal reflex image array data obtained for two eyes having keratoconus using the ocular instrument of FIG. 1 are shown. The array of images 91 and 92 and large eye images 93 and 94 taken from the camera for different positioned infrared LED's reveal Keratoconus in the form of shadows 95 and island areas 96 that asymmetrically appear in the images located about the central image 97. The difference in the appearance of the images in FIGS. 6(*a-b*) is due to the location, the shape, and the dimension of the irregular cornea protruding in the two KC eyes.

Figure 7A:
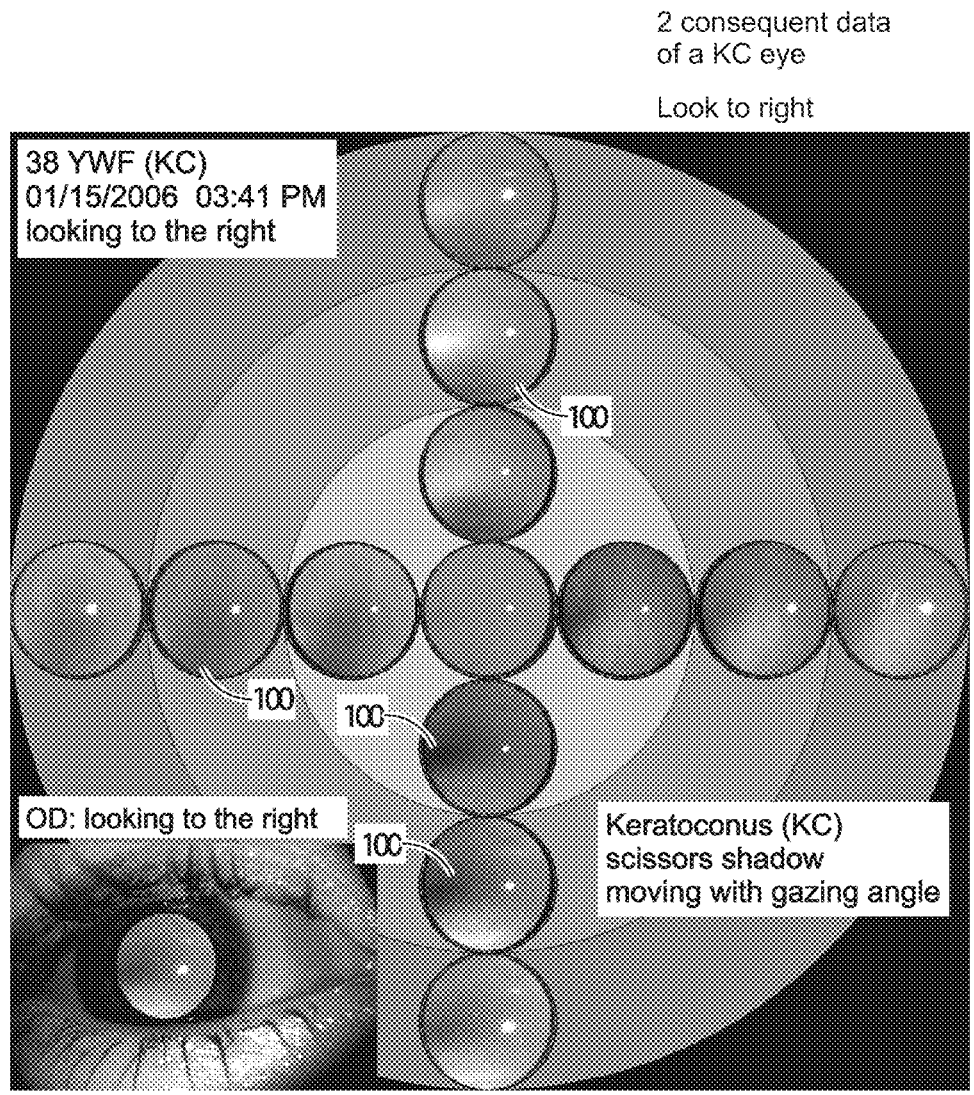
FIGS. 7(a) and 7(b) are illustrations showing the ability to detect ocular items of interest using multiple time dispersed infrared photorefractive image data obtained for an eye.
Figure 7B:
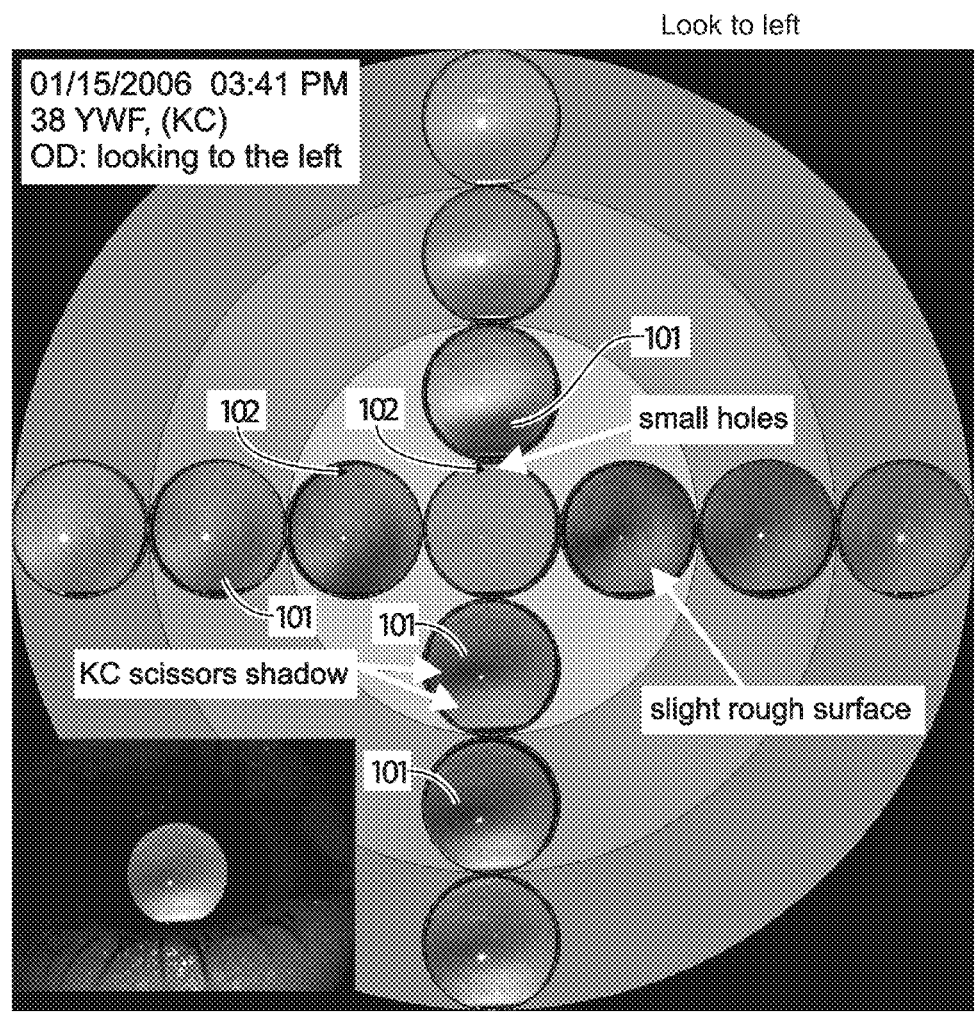

Referring now to FIGS. 7(*a*) and 7(*b*), illustrations showing the ability to detect ocular items of interest using multiple time dispersed photorefractive image data obtained for all eyes are shown. In FIG. 7(*a*) the individual is looking to the right and dark areas 100 are visible in several of the eccentric images. In FIG. 7(*b*), the individual is looking to the left and corresponding dark shadows 101 are visible in the corresponding eccentric images. The patient gazing angle can be determined through the Hirschberg method using the small bright spot of cornea reflection at the center of pupil. In addition, similar spots 102 are visible in several of the images taken while looking to the left that are not visible while the individual was looking right. These spots are most likely due to transient particles that have moved during the time between the acquiring of the images.

Figure 8A:
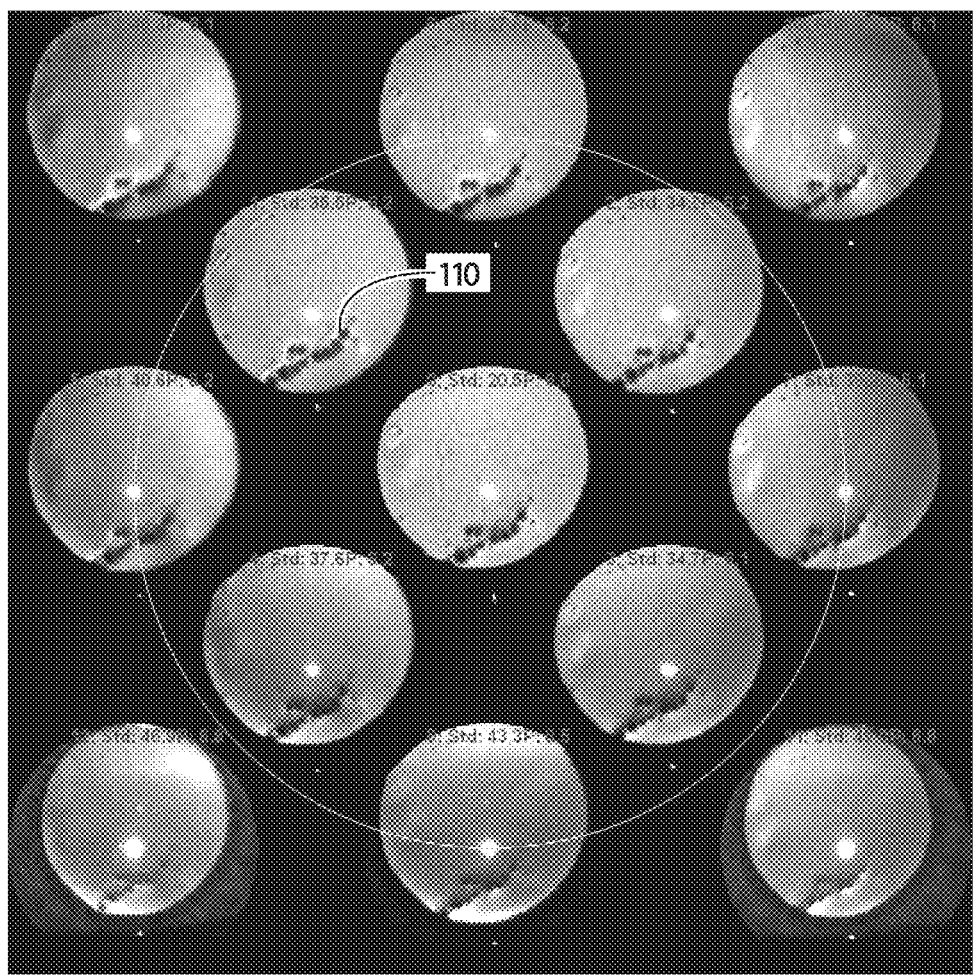
FIGS. 8(a) and 8(b) further illustrate the ability of an embodiment of the present invention top discriminate between transient and permanent aberrations.
Figure 8B:
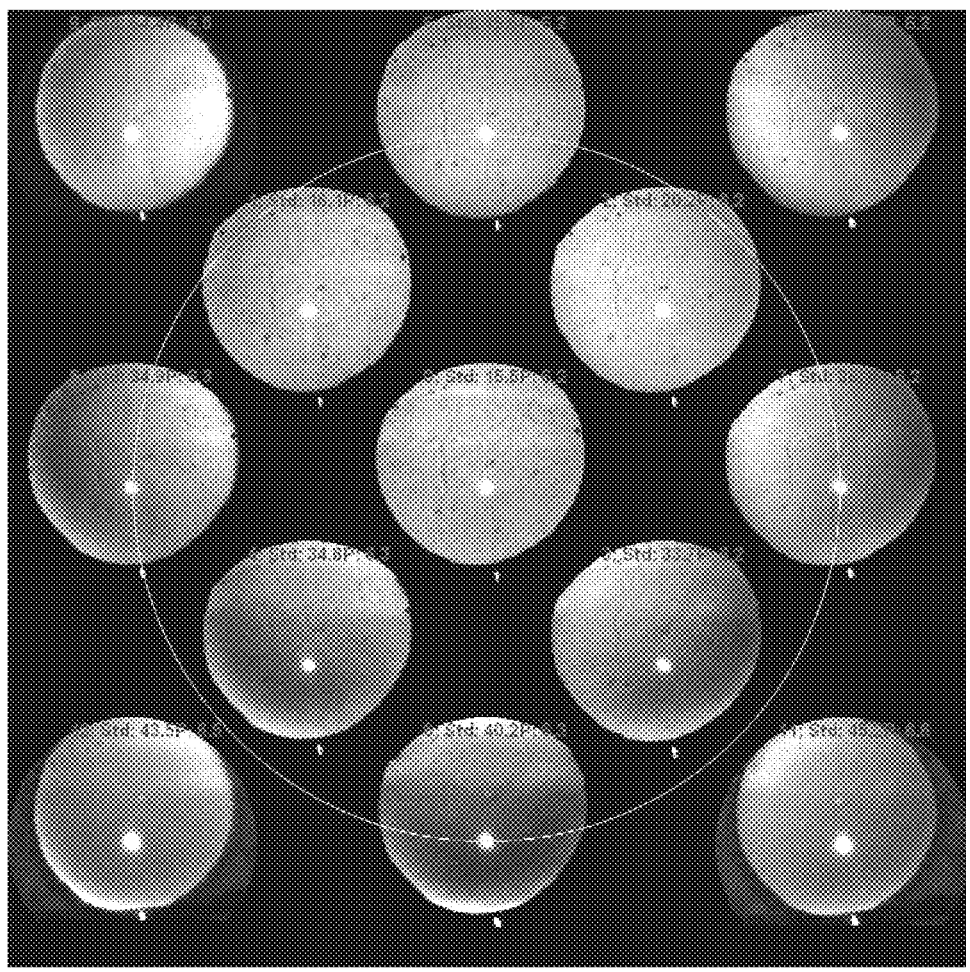

Referring now to FIGS. 8(*a*) and 8(*b*), the ability of an embodiment of the present invention to discriminate between transient and permanent aberrations is further illustrated. In FIG. 8(*a*), a series of spots 110 are visible in a number of the photorefractive eye images. However, in the images of FIG. 8(*b*), the spots 110 are gone. The images of FIG. 8(*b*) were acquired subsequent to the acquisition of the images of FIG. 8(*a*). Since the spots 110 are missing, it can be inferred that they represented a transient ocular condition in the patient.

Figure 9A:
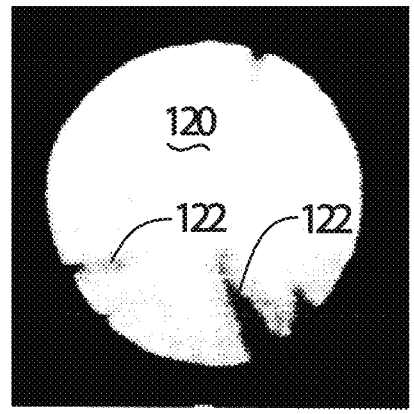
FIGS. 9(a) and (b) are illustrations of infrared photorefractive images of an eye taken with an ocular instrument constructed in accordance with an embodiment or the present invention.
Figure 9B:
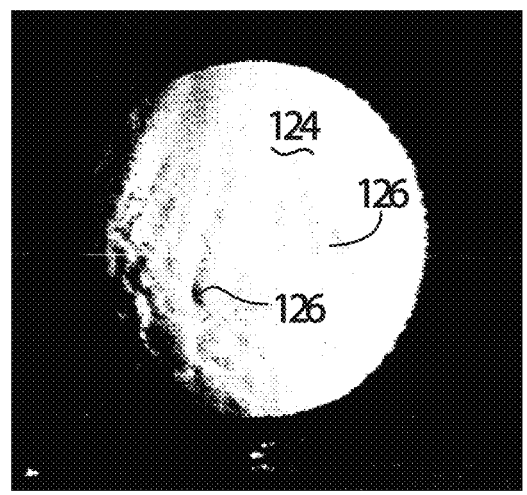

Photorefractive images produced in accordance with an embodiment of the present invention can be used in a similar fashion to analyze the time required for tear film breakup after a blink and therefore, to define an index of tear film quality. Referring now to FIGS. 9(*a*) and (*b*), photorefractive images of an eye taken with an ocular instrument constructed in accordance with an embodiment of the present invention are shown. The eye 120 of FIG. 9(*a*) has a cortex cataract 122 which appears as lines in the image. In the eye 124 of FIG. 9(*b*), the tear-film 126 on the eye can be observed as irregular groves in the image. A measurement of the tear-film's 126 break-up can be obtained with an instrument constructed in accordance with an embodiment of the present invention. In accordance with one method of doing so, a concentric image of an eye is obtained with a single LED lit three times per second for ten seconds and the images saved. The patient is instructed to blink and open their eye at the onset of the procedure and to hold their eye open for the 10 second period. The breakup of the tear film can be observed by examining changes in the appearance and location of the tear film over time. If there are no detectable signs of tear film breakup during the 10 second period, the patient does not have a dry eye condition according to accepted definitions. Currently, fluorescine eye drops or testing papers which are placed under the eye lid must be used to diagnose dry eyes. These procedures are intrusive and uncomfortable for the patient. Therefore, the present invention provides an improved way to diagnose and monitor patients having dry eyes and cortex cataracts.

Embodiments of the present disclosure can also be viewed as providing methods for performing an ocular examination. In this regard, one embodiment of such a method, among others, can be broadly summarized by the following steps: performing an automated photorefractive ocular examination procedure; analyzing the photo refractive ocular wavefront images to assess at least one ocular condition; and providing results from the analyzing step, where the screening procedure includes the steps of: adjusting the intensity or duration of the irradiation source and the settings of the image sensor or camera such that the photorefractive ocular images of an examinee are within a targeted range.

A preferred embodiment of the present invention provides a number of advantages over the prior art. First, since the procedure is noninvasive, it is very unlikely to result in any harm to the patient. In addition, by utilizing infrared radiation, which is invisible to an individual, as the light source, the system avoids the discomfort associated with present retinoscopes that utilize bright lights. There are also no chromatic aberration complications if a monochromatic NIR light source is used.

Other systems, methods, features, and advantages of the present disclosure will be or become apparent to those with skill in the art upon examination of the following drawings and detailed description. It is intended that all such additional systems, methods, features, and advantages be included within this description and be within the scope of the present disclosure. Thus, although there have been described particular embodiments of the present invention of a new and useful "ADAPTIVE INFRARED RETINOSCOPIC DEVICE FOR DETECTING OCULAR ABERRATIONS" herein, it is not intended that such references be construed as limitations upon the scope of this invention except as set forth in the following claims.

What is claimed is:

1. A device for detecting high order aberrations in ocular properties of a patient's eye, said device comprising:
    an array of infrared light sources comprising a central infrared light source and at least one eccentrically positioned infrared light source that can be individually activated to produce infrared light;
    an image sensor that detects infrared light and produces an image based upon said detected infrared light; and
    an optical beam splitter that is positioned to co-axially align a detection path from said patient's eye to said image sensor and an infrared illumination path from said central infrared light source to said patient's eye such that said infrared light from said central infrared light source is directed into said patient's eye, focused to a point on said patient's retina by optical elements of said patient's eye, reflected and scattered by said patient's retina and emitted from said patient's eye;
    wherein said image sensor receives infrared light reflected and scattered from said patient's retina and produces a photorefractive image of said patient's retinal reflex based on a spatial distribution of said infrared light received through an entrance pupil of said image sensor that is dependent upon any high order aberrations present in said ocular properties of said patient's eye; and
    wherein eccentrically illuminated photorefractive images of said patient's retinal reflex are produced by selectively activating an eccentrically positioned infrared light source in said array of infrared lights sources and detecting a distribution of said infrared light received through said entrance pupil of said image sensor in response to activation of said eccentrically positioned infrared light source.

2. The device of claim 1 wherein the optical beam splitter and the array of infrared light sources are positioned such that the distance between the optical beam splitter and array of infrared light sources is equal to the distance between the optical beam splitter and the optical entrance pupil of the image sensor.

3. The device of claim 1 further comprising a computer for storing multiple photorefractive images, instantaneously displaying said images for real-time review and digitally analyzing said images to identify ocular abnormalities.

4. The device of claim 1 further comprising a computer that processes said coaxially illuminated image to determine an illumination intensity to use for said array of infrared light sources when producing said eccentrically illuminated image.

5. The device of claim 1 wherein eccentrically illuminated photorefractive images of said patient's retinal reflex are further produced by adjusting an angular tilt of said optical beam splitter.

6. A device for detecting high order aberrations in ocular properties of a patient's eye, said device comprising:
   an infrared light source that produces infrared light;
   an image sensor that detects infrared light and produces an image based upon said detected infrared light; and
   an optical beam splitter that is positioned to co-axially align a detection path from said patient's eye to said image sensor and an infrared illumination path of said infrared light from said infrared light source such that said infrared light is directed into said patient's eye, focused to a point on said patient's retina by optical elements of said patient's eye, reflected and scattered by said patient's retina and emitted from said patient's eye;
   wherein said image sensor receives through an entrance pupil infrared light reflected and scattered from said patient's retina and based upon a detected spatial distribution of said received infrared light produces a photorefractive image of said patient's retinal reflex that is dependent upon any high order aberrations present in said ocular properties of said patient's eye;
   and wherein eccentrically illuminated photorefractive images of said patient's retinal reflex are produced by altering an angular tilt of said optical beans splitter.

7. A device for detecting a high order optical aberration in an eye of a patient, said device comprising:
   a two-dimensional array of infrared light sources wherein each of said infrared light sources can be independently activated to produce a pulse of infrared light;
   an image sensor that is positioned to receive infrared light that is reflected from said patient's eye and produce a photorefractive image of a retinal reflex intensity pattern based upon detected infrared light;
   an optical beam splitter that aligns a detection path from said patient's eye to said image sensor and an infrared illumination path of a said infrared light sources in said two dimensional array of infrared light sources to the patient's eye such that infrared light entering the patient's eye from each of said infrared light sources is focused on a different point on a retina, of said patient's eye by the optical elements of the eye, reflected and scattered by said patient's retina, and emitted from said patient's eye; and
   a computer system that activates a centrally positioned infrared light source with an illumination path that is coaxial with a detection path of said image sensor to produce a coaxial photorefractive image of said patient's retinal reflex intensity pattern and activates an eccentrically positioned infrared light source with an illumination, path that is eccentric to a detection path of said image sensor to produce an eccentric photorefractive image of said patient's retinal reflex intensity pattern;
   wherein said patient's retinal reflex intensity patterns are examined to identify any high order optical aberrations present in said patient's eye.

8. The device of claim 7 wherein said computer system further comprises software that automatically analyzes said patient's retinal reflex intensity patterns to identify high-order ocular aberrations.

9. The device of claim 7 wherein said computer system further comprises software that performs image correlation analysis between retinal reflex intensity patterns acquired at different times to differentiate between transient and stationary ocular conditions.

10. The device of claim 7 wherein said computer system automatically adjusts the intensity of said infrared light produced by said infrared light sources in said two dimensional array of infrared light sources for eccentrically illuminated photorefractive retinal reflex images based upon an intensity level of a detected reflectance when the patient's eye is coaxially illuminated with respect to a central axis of the image sensor.

* * * * *